United States Patent [19]

Mueller et al.

[11] Patent Number: 4,826,677

[45] Date of Patent: May 2, 1989

[54] PHARMACEUTICAL MATERIAL FOR THE TREATMENT OF PSORIASIS

[75] Inventors: Josef Mueller, Lindenfels; Hans-Ulrich Petereit, Darmstadt, both of Fed. Rep. of Germany

[73] Assignee: Röhm Pharma GmbH, Weiterstadt, Fed. Rep. of Germany

[21] Appl. No.: 33,248

[22] Filed: Apr. 2, 1987

[30] Foreign Application Priority Data

Apr. 11, 1986 [DE] Fed. Rep. of Germany ....... 3612305

[51] Int. Cl.$^4$ ...................... A61K 31/74; A61K 31/78
[52] U.S. Cl. ..................................... 424/78; 514/680; 514/863; 424/81
[58] Field of Search ......................................... 514/863

[56] References Cited

U.S. PATENT DOCUMENTS 4,007,271 2/1977 Robertson ........................... 514/863
4,496,588 1/1985 Bey ..................................... 514/863

FOREIGN PATENT DOCUMENTS 2515045 4/1983 France .
1504007 2/1978 United Kingdom .
2116423 4/1983 United Kingdom .
2145627 6/1985 United Kingdom .
83/00084 4/1983 World Int. Prop. O. .

OTHER PUBLICATIONS

Martindale, Extra Pharmacopolia 28th Ed. 1968 Pharma. Press London, p. 494.

Primary Examiner—Joseph L. Schofer
Assistant Examiner—Peter F. Kulkosky
Attorney, Agent, or Firm—Oblon, Fisher, Spivak, McClelland & Maier

[57] ABSTRACT

The invention relates to pharmaceutical materials for local and non-irritating therapy for psoriasis, containing antipsoriatic ingredients. The pharmaceutical material is a liquid preparation of film-forming polymers and antipsoriatic ingredients, with which the psoriasis affected skin area can be covered and treated in situ with a medicated film or foil formed at the treatment site. Dithranol and/or glucocorticoid in combination with keratolytically acting urea are preferred for use as antipsoriatic ingredients.

12 Claims, No Drawings

PHARMACEUTICAL MATERIAL FOR THE TREATMENT OF PSORIASIS

BACKGROUND OF THE INVENTION

1. Field of the Invention

The invention relates to a liquid pharmaceutical preparation for the local treatment of psoriasis containing known antipsoriatic active ingredients, in which the medicines therapeutically take effect from a film located on the affected skin area.

2. Discussion of the Background

In treating psoriasis, a dermatosis of yet unexplained origin, one is generally instructed to apply drugs topically such as salicylic acid, vitamin A-acid, glucocorticoids, and more recently with relatively good success, dithranol (1,8,9-anthracenetriol) or acyl derivatives thereof. The formulations to be used are limited to the most common preparations such as, for example, solutions, creams, and salves, in which the manner of application for the dermatherapy is practically predetermined. The use of the therapeutic preparations which generally contain some fat, such as dithranol-salicyclic acid vaseline, a paste-like preparation, are very time consuming for the patients and involve more difficult procedures. Large surface area applications can therefore be preformed only on inpatients, and involves soiling large amounts of laundry and clothing.

By combining the use of urea and the application of dithranol, as according to EP-A No. 6,724, the psoriasis therapy is improved. Preparations of this kind, having for example 0.1% dithranol in a 17% urea salve base, are known, i.e., Psoradrate (see D.M. Wiliamson in Clin. Exp. Dermatol., vol. 8, pp. 287–290 (1983)). Urea, which is known for its keratolytic characteristics, disrupts the epidermis for a more rapid and therefore more effective penetration of the active drug.

In treating particularly resistant strains of psoriasis, the locations which are coated with salve, are covered with waterproof bandages. A sealed moist chamber is thus formed which allows the skin to swell and facilitates penetration of the medicine into the deeper layers.

Medicated self-adhering plasters containing medicines may also be used. To allow for better skin respiration, they are usually perforated and applied to an elastic material. See Ulmanns Encyclopedia of Technical Chemistry, 4th Ed., vol. 4, pp. 24–26. Non-perforated self-adhering bandages for topical therapy with glucocorticoids are known in the form of foils containing the halogenated corticoid fluorandrenolone and having an adhesive layer.

Polymer films containing anthraline (dithranol) or anthraline derivatives as medicines for treating skin injuries such as psoriasis, are disclosed in French Pat. No. 2,515,045. These films are manufactured prior to use from an appropriate solution by being cast in a teflon mold and dried for 15 hours. Molded elements of this type are difficult to apply to affected skin areas.

A more direct method of producing a medicated film on the skin for transdermal application is described in Japanese Kokai Tokkyo Koho 60 16922 (Chem. Abstr. 102, 226041a). According to this reference, a viscous solution containing the pharmaceutical materials is applied to the skin which is then sprayed together with a film-forming polymer solution. This two-stage method for constructing a topical therapeutic system is very awkward, however, and is difficult to accept as a long, extended therapy for the patient.

SUMMARY OF THE INVENTION

Accordingly, one object of the present invention is to provide a pharmaceutical material for the treatment of psoriasis which occupies as small an area as possible on non-affected body parts.

A further object of the invention is to provide a pharmaceutical material which is easily applied and which minimizes patient discomfort.

A further object of the invention is to provide a pharmaceutical material which provides uniform dosing of medicines without spreading to healthy skin areas and thereby avoids unnecessary skin irritation.

Still another object of the invention is to provide a pharmaceutical material which avoids the soiling of large amounts of laundry and clothing.

These objects and other objects of the invention which will become apparent from the following specification have been achieved by the present pharmaceutical material for local treatment of psoriasis, comprising: a liquid preparation of at least one film-forming polymer and at least one anti-psoriatic compound.

DETAILED DESCRIPTION OF THE PREFERRED EMBODIMENTS

It has been discovered that closely encircled, psoriasis affected skin areas can be easily covered with medicine-containing films by applying new film-forming polymer solutions or polymer dispersions which contain medicines either dissolved or suspended in the liquid pharmaceutical material. Accordingly, it is now possible to cover and treat the psoriasis in situ with a medicated film or foil which is conveniently formed at the treatment site from a solution or dispersion.

The new preparations according to the invention, which contain film-forming, physiologically inert polymers and antipsoriatic medicines in liquid form, are suitable for the in situ production of the medicinally effective films or foils. The film-forming polymers and the medicines are either dissolved or suspended in the liquid medium, which itself must not be an irritant and not of concern from a physiological standpoint, such as water or a mixture of water with ethanol and/or isopropanol or either of these solvents alone.

As is common for therapeutic purposes, the self-forming films or foils should be as tear-resistant as possible, supple, water or vapor permeable, as well as tolerated by skin and capable of good adhesion to the skin. Suitable polymers which fulfill these requirements in the pharmaceutical materials according to the invention can be natural polymeric materials, semi-synthetic or synthetic polymeric materials. Examples include polyethylene, polyurethane, polyvinyl-chloride, polyvinyl alcohols, polyvinyl acetate, poly(meth)acrylates or mixtures thereof and particularly their copolymers. Also suitable are cellulose derivatives, such as cellulose acetate or methylcelluloses such as Methocel ®.

The polymers can be present as solutions or as dispersions of, for example, 5 to 70% by weight, particularly 10 to 50%, in the preparations and can be employed as such during manufacture of the preparations. Other polymers within the scope of the invention are acrylic resin dispersions, which are technically important products belonging to the class of physically drying film-forming materials, as well as copolymers of methacrylic esters and acrylic esters and any other suitable vinyl monomers. Suitable solutions and dispersions of acrylic resins are readily available such as, for example, Eudragit ®.

By including functional groups through copolymerization with appropriately constructed monomers, polymers of a cationic or anionic character can be produced and used in accordance with the invention in addition to non-ionic polymers.

The substances known as antipsoriatic medicines, such as allantoin, tar products, chrysarobin, dithranol, dithranol derivatives, vitamin A, undecylenic acid, and glucorticoids, such as fluorandrenolone, are present in the preparations in dissolved or finely suspended form. The simultaneous presence of urea in the materials according to the invention has a particularly favorable effect. Therefore, the materials according to the invention may contain urea, either in dissolved form or in suspension in the desired degree of dispersion.

The content of antipsoriatic medicine in the pharmaceutical material is from 0.1 mg to 200 mg per g of polymer-solid in solution or suspension.

The content of urea preferably is 50 to 250 times the weight of the antipsoriatic medicine. In its suspended form, urea is generally used in a therapeutically allowable quality and with a particle size in the range from 1 to 50 micron. The size of suspended medicine particles preferably lies in the same range.

The solutions or dispersions according to the invention are applied to the affected skin area, if necessary after a previous shaking, from a tube, with a brush or something similar or by spraying. Spraying offers a preferable application method when a solution is used.

The film formation from the macro-molecular materials begins immediately as the solvent, such as water and/or alcohols evaporates out of the solution or dispersion applied to the skin. Within a few minutes, non-stick films or foils have formed containing the embedded active medicinal ingredients or ingredient combinations, which from there pass to the effected site through diffusion. The thickness of the film or foil layers generally lies in the range of 20 to 400 microns and depends on the desired duration of the application. At the end of the application period the foil is removed by simply pulling it from the skin.

The preparations according to the invention provide pharmaceutical materials with which very effective therapeutic conditions are simply and rapidly created on skin areas to be treated, particularly those affected by psoriasis. The uniform dosing of the medicines without spreading onto healthy skin areas avoids unnecessary skin irritations. In addition, the discoloration of underclothes and clothing caused by dithranol is avoided. Through selection of a suitable polymer and careful addition of auxiliary materials such as softeners, very elastic films with good adhesion to the skin can be produced which also achieve good therapeutic success even on problematic areas of the skin, such as on the large body joints.

The good permeability of the polymer film to moisture increases the tolerability of the therapy system due to minimal interference with the natural moisture content of the skin. The materials according to the invention provide significant progress relative to the prior art due to their simplicity of use, namely the production of medicated films by casting in a mold with long drying times or the use of at least 2 different solutions.

Other features of the invention will become apparent in the course of the following descriptions of exemplary embodiments which are given for illustration of the invention and are not intended to be limiting thereof.

EXAMPLES

EXAMPLE 1

100 g of polyvinyl alcohol is finely dispersed in 200 g of ethanol under intensive stirring and is mixed with 500 g of pH 5.0 citrate buffer (0.027 molar). This mixture is heated to 80° C. for about 20 minutes under continued stirring until the polymers are completely dissolved. After cooling to 40° C., any loss due to evaporation is replaced. 17 g of urea and 2 g of sodium dithionite are dissolved in 180.9 g of citrate buffer (pH 5.0) and 0.1 g of dithranol is uniformly suspended therein by means of intensive stirring. Subsequently, both liquids are mixed, so that a yellow colored, highly viscous liquid is formed which can be poured into tubes.

After application to the skin, the gel-like liquid dries within 20 minutes to a flexible, thin, well adhering film, which after a certain period of time, for example overnight, can be removed by simply pulling it off.

EXAMPLE 2

While being stirred with a propellor stirrer, 2.7 g of citric acid monohydrate and 58 g of urea dissolved in 779 g of Eudragit ® E 40 D are mixed with 10 ml of a 1% sodium sorbate solution and adjusted with 7 g of 3N sodium hydroxide to a pH value of about 5.

A solution of 15 g of sodium dithionite in 100 g of distilled water is heated to 80° C., mixed with 17 g of Methocel ® E5 and stirred during cooling until completely dissolved.

Subsequently, both liquids are mixed and stirred for about 1 hour until a uniform mixture is achieved.

The ready-to-use packaging takes the form of 100 ml brush applicator bottles.

For therapy, the medicated thickened dispersion is applied to the affected skin areas by means of the brush. Within about 15 seconds the drying process produces an elastic, well adhering film which can simply be pulled off at the end of a period of therapy.

EXAMPLE 3

15 g of Span ® 40, lipophilic tenside (sorbitane palmitate), 30 g of glycerin and 770.3 g of citrate buffer at pH 5 are heated to 80° C. and stirred until uniform distribution is achieved. Under continued stirring, 150 g of Methocel ® E5 is added and cooled to room temperature. Subsequently, 33.2 g of urea and 10 g of a 1% sodium sorbate solution are added and stirred until fully dissolved.

The application to affected skin areas and use characteristics are the same as in Example 1.

EXAMPLE 4

700 g Eudragit ® L 30 D is mixed with a solution of 33 g of sodium hydroxide in 151.5 g of distilled water and stirred until the polymers are completely dissolved. Then 36 g of polyethylene glycol 6000, 10 g of sodium dithionite, 35 g of urea and 10 g of a 10% sodium sorbate solution are added in succession and the mixture is stirred until clear after each addition.

Subsequently, a suspension of 0.5 g of dithranol in 24 g of glycerin is uniformly distributed in the mixture.

Further processing and application is in accordance with Example 1.

EXAMPLE 5 100 g Eudispert ® nv (powdered polymethacrylate) is suspended in 500 g of distilled water, allowed to swell for 30 minutes, mixed with 196 g of 3N sodium hydroxide and heated to 70°–80° C. while being stirred until the solution is clear.

After cooling to room temperature, evaporated water is replaced and the following components are admixed and dissolved in succession: 30 g glycerol, 2 g ascorbic acid, 3 g citric acid monohydrate and 15 g urea. Subsequently, 10 g of sodium dithionite is dissolved in 133.6 g of water, 0.3 g of dithranol is suspended therein and this suspension is uniformly distributed through the polymer solution. As a preservative, 10 g of a 10% sodium sorbate solution is also added.

The manner of application and use characteristics of the preparation correspond to those in Example 2.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A pharmaceutical material for topical treating of psoriasis, consisting essentially of:
   a liquid preparation of 5–70 wt.% of at least one film-forming polymer selected from the group consisting of polyethylene, polyurethane, polyvinyl chloride, polyvinyl alcohol, polyvinyl acetate, poly(meth)acrylate and copolymers thereof and at least one anti-psoriatic compound, wherein a thin, well adhering film is formed by said preparation, said film being removable by pulling it from the treated area.

2. The pharmaceutical materials of claim 1, werehin said film-forming polymer is polyvinyl alcohol or poly(meth)acrylate or copolymer thereof.

3. The pharmaceutical material of claim 1, wherein said liquid preparation is a solution comprising a solvent, said film-forming polymer and said antipsoriatic compound.

4. The pharmaceutical material of claim 1 wherein said liquid preparation is a dispersion of said film-forming polymer and wherein said antipsoriatic compound is dissolved or suspended in said dispersion.

5. The pharmaceutical material of claim 1, said film-forming polymer comprises about 1–70 wt.% of said liquid preparation.

6. The pharmaceutical material of claim 5, wherein said film-forming polymer comprises between about 10–50 wt.% of said liquid preparation.

7. The pharmaceutical material of claim 1, wherein sa.id film-forming polymer is capable of forming of a water or vapor permeable film.

8. The pharmaceutical material of claim 1, wherein said liquid preparation comprises from about 0.01–20 wt.% of said antipsoriatic compound, calculated according to the dry film forming polymer.

9. The pharmaceutical material of claim 1, further comprising urea.

10. The pharmaceutical material of claim 9, wherein said urea is present in a uniform distribution.

11. The pharmaceutical material of claim 10, wherein said urea is present in amounts of about 50–250 times the weight of said antipsoriatic compound.

12. The pharmaceutical material of claim 1, wherein said antipsoriatic compound comprises a glucocorticoid, dithranol or a mixture thereof.

* * * * *